United States Patent
Perle et al.

[11] 3,980,131
[45] Sept. 14, 1976

[54] STERILIZER FOR CULTURE MEDIA AND LABORATORY WARE

[75] Inventors: Abe J. Perle, Verona; David Freedman, Highland Park, both of N.J.

[73] Assignee: New Brunswick Scientific Co., Inc., New Brunswick, N.J.

[22] Filed: May 8, 1975

[21] Appl. No.: 575,569

[52] U.S. Cl. ................................. 165/61; 21/94; 21/97; 165/30; 165/54; 165/163; 165/169
[51] Int. Cl.² ........................................ F25B 29/00
[58] Field of Search ................. 122/32, 33; 165/14, 165/26, 30, 32, 39, 53, 54, 56, 61, 106, 157, 160, 163, 169; 21/94, 97; 23/290

[56] References Cited
UNITED STATES PATENTS

| | | | |
|---|---|---|---|
| 2,631,015 | 3/1953 | Probst | 165/169 |
| 2,713,702 | 7/1955 | Jewell | 21/94 |
| 2,772,860 | 12/1956 | Nelson | 165/169 |
| 2,987,605 | 6/1961 | Brandl | 122/32 |
| 3,197,076 | 7/1965 | Chamblee | 165/169 |
| 3,704,691 | 12/1972 | Brandl | 122/33 |
| 3,739,842 | 6/1973 | Whalen | 165/169 |
| 3,910,761 | 10/1975 | Hopkins | 21/94 |
| 3,910,812 | 10/1975 | Kanedo | 165/61 |
| 3,926,250 | 12/1975 | Engwall | 165/169 |

Primary Examiner—Charles J. Myhre
Assistant Examiner—Daniel J. O'Connor
Attorney, Agent, or Firm—Blum, Moscovitz, Friedman & Kaplan

[57] ABSTRACT

A vessel, containing a culture medium or laboratory ware, is brought rapidly to sterilization temperature by circulating a mixture of steam and superheated water through a closely spaced jacket. The mixture of steam and superheated water is generated in a portion of the sterilizer which is exterior to the jacket and said mixture is circulated without the use of a pump. The sterilizer can be made in sizes small enough for bench-top operation and the sterilization procedure can be carried out with automatic control.

18 Claims, 7 Drawing Figures

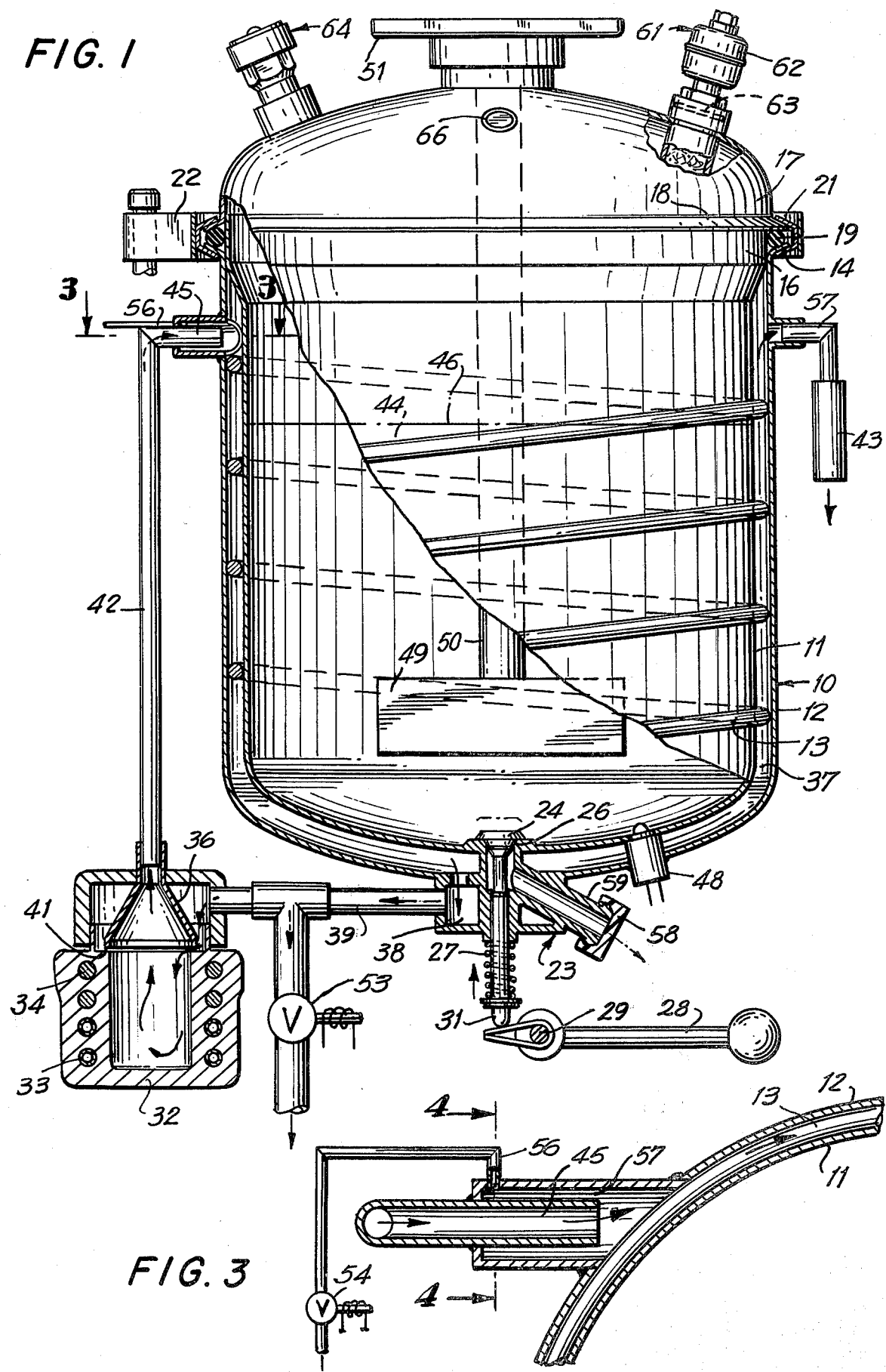

STERILIZER FOR CULTURE MEDIA AND LABORATORY WARE

BACKGROUND OF THE INVENTION

While autoclaving is an old procedure for which many types of structures have been designed, in general, the equipment is large, relatively expensive and relatively slow in operation. A particular difficulty is encountered in the sterilization of culture media such as agar where it has usually been the practice to prepare an agar solution in a glass flask and then to place the flask in an autoclave. Since it is difficult, if not impossible, to provide for stirring under such circumstances, heat transfer through the medium has been poor. This results in part from the fact that glass is a relatively poor heat transfer medium and in part from the fact that the agar solution is viscous so that heat transfer by convection is likewise poor.

Depending on the size of a flask, the contents of which it is desired to sterilize, the procedure may require as long as 2 to 3 hours. Since agar, as well as other culture media, is heat-labile, some degradation of the medium occurs. Consequently, it would be highly desirable that means be provided for raising the temperature of the medium to the desired level very quickly and insuring that the entire contents of the vessel stay at the requisite uniform temperature for an adequate length of time, while avoiding the degradation which is consequent on prolonged heating at sterilization temperature.

Attempts to meet this objective by the use of metal vessels fitted with electrical heaters have been made. However, local hot-spots can develop so that the temperature of the vessel wall may far exceed the 250°F (121°C) sterilization temperature. Moreover, if part of the electrically heated vessel loses contact with the solution in the vessel as the level drops due to removal of solution, or if the vessel is only partly filled, then local overheating and charring of heat-labile medium will occur.

Another problem encountered with conventional equipment arises from the fact that considerable heat is stored in the unjacketed dome or head of the vessel. After sterilization is complete and during the cooling-down period, some of this heat is radiated to the surface of the liquid in the vessel. Unless an agitator is present to provide adequate mixing, the medium at the surface of the solution can be seriously degraded.

Most sterilization systems in which the quantity of solution treated is larger than will be used in a single culture vessel require a dispensing port. Unless the port is properly jacketed, the material in the port will not be sterilized. Consequently, means for taking any solution in the dispensing portion of the system up to sterilization temperature and maintaining it there for the appropriate length of time must be provided.

As is evident from the aforenoted presentation, what is needed is a sterilizer which can be rapidly brought to sterilization temperature, which is free of hot-spots and which can rapidly be brought down to dispensing temperature and which insures that all of the culture medium in same is aseptic and free of degradation as the result of overheating.

SUMMARY OF THE INVENTION

In accordance with the present invention, apparatus for sterilizing a culture medium includes a vessel having a removable head which can be sealed thereto by an appropriate clamp. The entire side and bottom of the vessel is surrounded by a close-fitting jacket spaced therefrom by a wire spiral. A mixture of steam and water is supplied to the jacket by means of a gas-lift arrangement powered by electric heating coils. The coils bring water to a boil in a small chamber at the bottom of a column and a mixture of water and steam rise through the column and enter the jacket near the top thereof. The water than runs down the jacket in a spiral path, guided by the wire which separates the jacket from the vessel.

The jacket is fitted near the top thereof with a pressure-operated valve which opens when the internal jacket pressure reaches the operating limit, usually, 35 psig. The valve thus serves the purpose of providing blow-off protection to the jacket and vessel during initial jacket filling from a higher pressure water service. If also allows the by-pass of excess jacket water resulting from the volumetric expansion of the enclosed water upon heating. By limiting jacket pressure to 35 psig, (136°C), excessive heating rates of the contained medium are precluded by the limited temperature differential existing during the controlled sterilization cycle.

The dome is fitted with a vent which permits the passage of air but not of liquid. As the vessel comes up to temperature, air in the solution and in the ullage above the liquid is vented. When the system is cooled, air is allowed to enter the vessel through a hydrophobic filter which prevents the passage of water and of particles greater than about $0.8\mu$, thereby preserving the contents from contamination by water droplets, bacteria or particulate-borne viruses. The dome is also fitted with a motor stirrer holding a paddle for agitation of the solution.

The vessel is fitted at the bottom thereof with a dispensing valve through which sterilized solution can be drawn after the temperature of the system has been dropped, usually to about 46°– 50°C. The dispensing valve is cored, the core being connected to the jacket so that superheated water must pass through the core to return to the vessel within the heating coils. As a result, the contents of the valve are maintained in aseptic condition.

A cooling water supply line and a drain line for introducing cooling water into the jacket and removing same from said jacket are provided for dropping the temperature of the vessel and its contents rapidly at the end of the sterilization period. The contents of the vessel are then maintained at the dispensing temperature, usually 46°C, by use of a low wattage heating coil to provide boiling water in controlled amount and cooling water introduced intermittently into the jacket.

The clamp which holds the dome to the vessel is removable by swinging a handle away from the vessel. A bimetal device is so arranged that the handle cannot be swung away from the vessel when the temperature of the contents is above 100°C, the purpose being to prevent inadvertent vessel opening with possible operator harm, once the pressure in the vessel exceeds atmospheric pressure.

An automatic controller receives a signal from a sensor in the bottom of the vessel and controls the heat input to the heating coils and the flow of cooling water so as to take the vessel through a cycle consisting of rapid heat-up to sterilization temperature, maintaining the temperature for a preset length of time, dropping the temperature rapidly to dispensing temperature and then holding the system at dispensing temperature.

Where the system is to be used for sterilization of laboratory ware, a second head is provided for the tank, said second head being free of stirring equipment. When sterilizing laboratory ware, the vessel itself may either be free of water or may contain water. When it is free of water, heat transfer to the vessels takes place mostly by radiation, a relatively slow process at sterilization temperature. Consequently, it is preferable to operate with the ware suspended over water.

Accordingly, an object of the present invention is an apparatus which can rapidly sterilize a culture medium or laboratory ware and which can rapidly be brought down to dispensing temperature and maintained at this temperature when a culture medium is to be dispensed.

Another object of the present invention is an apparatus which can be brought to sterilization temperature rapidly by injection of superheated water and steam into a jacket surrounding the sides and bottom of same.

A further object of the present invention is an apparatus which can be put through a sterilization cycle quickly without the use of a mechanical pump or heating coils in contact with the wall of the sterilization vessel.

An important object of the present invention is an apparatus for rapid sterilization which can be made in a variety of sizes ranging from one small enough to be characterized as bench-top.

A significant object of the present invention is an apparatus which can be put through a sterilization and dispensing program automatically.

Yet another object of the present invention is a sterilization apparatus which provides for sterilization of culture medium in a dispensing valve.

Still another object of the present invention is a sterilization apparatus having a closely fitting jacket to provide for rapid flow of heating and cooling fluid therethrough and thereby to provide rapid heating and cooling of the contents of the vessel in said jacket.

Yet a further object of the present invention is a method of sterilizing a culture medium rapidly and dropping the temperature of same rapidly to dispensing temperature.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is an elevational view in partial section of a sterilization apparatus in accordance with the present invention;

FIG. 3 is a top view in partial section of said apparatus showing lines for supplying hot and cold water to the jacket of the sterilization vessel;

DESCRIPTION OF THE PREFERRED EMBODIMENTS

Figure 4:
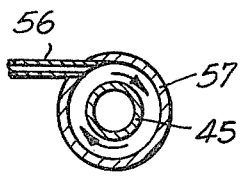
FIG. 4 is a view taken along line 4 — 4 of FIG. 3.

While sterilization apparatus in accordance with the present invention can be made in a wide range of sizes, it is particularly useful in the size which may be described as bench-top. Accordingly, the various fittings will be described in terms of an apparatus of this size, but it is to be understood that modification of the apparatus in ways known to those skilled in the art will make it possible to construct sterilization apparatus of any desired size. Moreover, it is to be noted that while the present apparatus will be described primarily in terms of sterilization and dispensing of culture media, it can be used for any system such as fermentation, for instance, where it is desired that the temperature of a vessel be quickly and reliably put through a sequence of temperatures, or a temperature profile, with high precision. The method of control described herein makes it possible to control the temperature of the contents of a vessel within ± 0.5°C with ease.

The sterilizer in accordance with the present invention is shown in partial section in FIG. 1 where a vessel and its jacket are indicated generally by the reference numeral 10. Vessel 11 and its jacket 12 are conveniently made by hydroforming stainless steel in the form of shells, the vessel fitting within the jacket. Vessel 11 is expanded at its upper extremity to form a close fit with the inner diameter of jacket 12. In a preferred embodiment, a wire 13 is helically wrapped and tack-welded to the exterior of vessel 11 to provide a helical path for liquid between vessel 11 and jacket 12. However, any path in which the liquid makes contact with a major portion of the exterior of vessel 11 to effect heat-exchange would be acceptable. The top edge 14 of jacket 12 is outwardly flanged and jacket 13 is brazed to outwardly expanded upper extremity 16 of vessel 11 and to wire 13. It should be noted that the entire apparatus is so constructed that all parts which are permanently sealed together are joined in one furnace-brazing operation.

Domed cover closure 17 also has an expanded edge 18 for forming a seal with flange 14 by means of O-ring 19. The seal between mating edges 14 and 18 is effected by "Vee" clamp 21 which is locked into position by means of toggle 22.

A dispensing valve indicated generally by the reference numeral 23 is furnace-brazed into vessel 11 and jacket 12 to maintain the spacing therebetween. Valve head 24 is normally positioned in seat 26 as the result of biasing by spring 27. To open valve 23 for dispensing of the contents of vessel 11, handle 28 is rotated in clockwise direction around shaft 29 to displace valve stem 31 upwardly.

The quick response in the temperature of the present apparatus to control effort is due in large part to the fact that the heat input system operates on an unusually small quantity of water, the system depending on flash electrical heating which provides both heat to the vessel and circulation of tempered water through the jacket 12. Boiler 32 is heated by high wattage coil 33 and low wattage coil 34. Conveniently, boiler 32 is cast of aluminum with both heating coils embedded therein. In the embodiment shown in FIG. 1, a tapered cap 36 is positioned over the top of boiler 32 with enough clearance therebetween so that water from jacket space 37 can pass through core space 38 of cored valve 23 and conduit 39 and finally through gap 41 between cap 36 and boiler 32 to re-enter boiler 32.

As jacket water enters the upper side entry of boiler 32 it is immediately heated by the high wattage density heater, forming a local pocket of superheated water and steam at the ambient pressure existing within the jacket circuit. The steam pocket formed attempts to drive the water in the heater back through side entry arm 39 as well as up through vertical riser tube 42. Since the inertia and effective resistance to flow through arm 39 and the spiral path in jacket space 37 is much greater than through riser tube 42, the steam generated drives water at boiling temperature through riser tube 42 causing the water to be injected at fairly high velocity into tangential jacket side-arm entry 45 (FIG. 3). Once the steam pocket has been blown through riser tube 42, the heater cavity is momentarily empty and the head of water in the jacket causes a slug of water to flow through the side arm 39 and into boiler 32. In this manner, a cyclical pumped stream of steam in superheated water is caused to flow through the vessel jacket as long as the heater is operating at high wattage input. Rupture of the jacket by uncontrolled thermal expansion of the water within is prevented by a sensitive inverted relief valve 43 which by-passes to drain the volume increase of the water in the jacket which results from heating same. Valve 43 also maintains sufficient pressure head in jacket space 37 to limit steaming. Since the entire vessel jacket and heater circuit is a closed loop, its ambient internal pressure has no effect on the circulation process previously described, except to raise the boiling temperature of the water to a value commensurate with the ambient internal jacket pressure. The pressure at which relief valve 43 vents can be arbitrarily selected so that the maximum temperature which the water in the jacket circuit may reach does not exceed a pre-selected value. This can be extremely important where the upper temperature of a heat-labile culture medium must be limited to prevent degradation. Consequently, where an extremely heat-labile medium is being processed, sterilization can be carried out for a slightly longer time period at lower temperature e.g. 110°C, set by adjustment of temperature controller 47, and peak jacket-water circulating temperatures can be reduced accordingly by resetting relief valve 43 to a lower venting pressure.

While the explanation presented above for the circulation of water and steam upwardly through riser tube 42 is based upon the difference in impedance between the riser tube 42 and gap 41, another factor also may enter. This is the fact that a mixture of steam and water has a lower density than that of water alone. Consequently, in accordance with the well-known operation of a gas lift, the lower density of the mixture of water and steam in riser tube 42 than of water alone in jacket space 37 could account for circulation in the direction specified. However, it is likely that the gas-lift effect is only a factor rather than the complete cause since the mixture of water and steam enters jacket space 37 at a substantial velocity. The operation of a gas-lift is generally more moderate.

Figure 6:
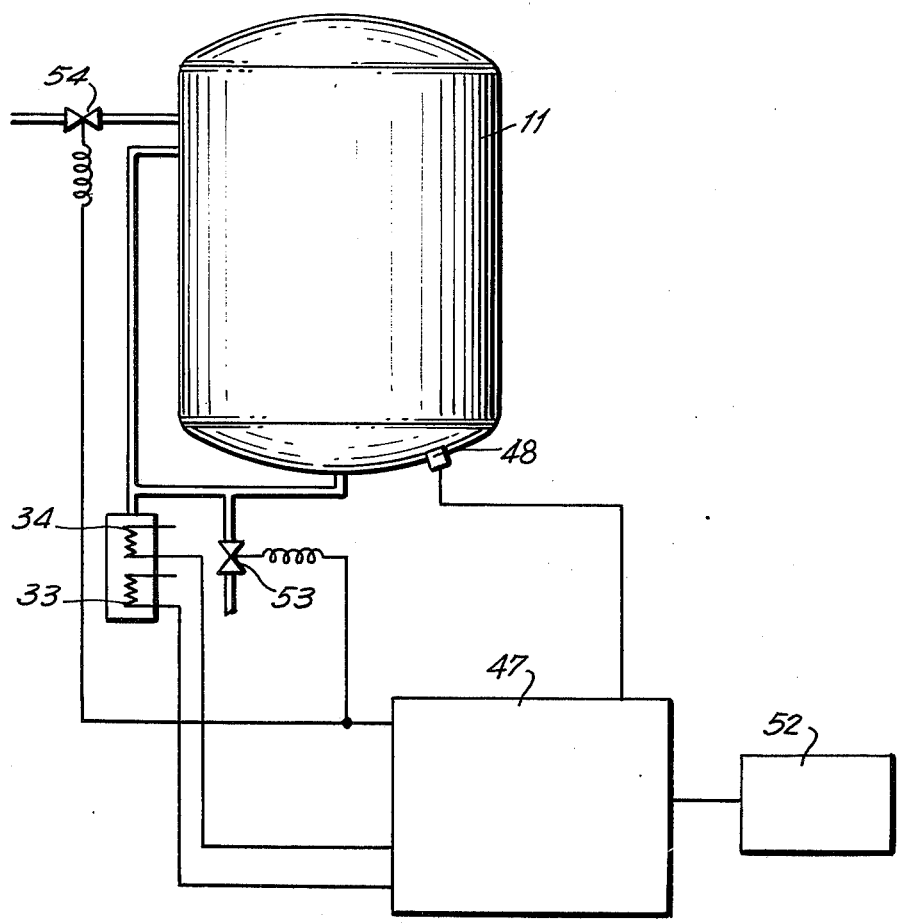
FIG. 6 is a diagram showing achematically the means for controlling the course of the temperature of the sterilization vessel during a sterilization and dispensing sequence.

The temperature of the medium 44 having the top surface 46 in vessel 11 is controlled by controller 47. The temperature of the medium 44 is read by sensor 48 which is preferably a thermister connected into a bridge circuit (not shown) which is part of controller 47. The control circuitry, when the vessel reaches a preset sterilization temperature effects a control action which starts a preset sterilization timer, such a timer being a simple form of programmer, indicated in FIG. 6 by the reference numeral 52. At the same time, the wattage output to the larger heating element 33 is reduced by the action of a solid state device (phase controller, not shown) to approximately one-half its starting value. The circuitry controller 47 is such that heater 34 remains on constantly while the reduced current to the high wattage heater 33 is turned on and off upon demand of the temperature control circuitry. By this means a combined wattage input is maintained during "on" control periods which is sufficient to provide protracted thermo-ram inertia pumping of the heating fluid through the jacket 12. During "off" control periods the low wattage heater provides enough boiling action for heater water circulation at a low rate. The net result of these two alternating modes of heating results is very close band-width temperature control of the medium within the vessel.

The jacket gap provided by the wire spiral 13 is preferably between 0.0625 and 0.1875 inch. Consequently, the mass of water in the jacket is very low, and temperature response is very rapid. In a preferred size, the jacketed height of liquid in vessel 11 is 8 inches and the outer diameter of vessel 11 is 7 inches. The distance between turns of wire 13 is between 1 and 2 inches and preferably is about 1⅜ inches. With a vessel of these dimensions, the vessel and its contents reach sterilization temperature in about 20 minutes. Heat transfer is aided by rotation of shaft 50 on which is mounted paddle 49. Shaft 50 passes through gland 51 and is driven by a motor (not shown).

Programmer 52 can be set to hold the vessel at a pre-selected sterilization temperature for a pre-selected time. As aforenoted, a sterilization timer starts running when the vessel reaches sterilization temperature. At the end of a preselected interval, usually about 15 minutes, a relay action shuts off high wattage heater 33 and opens jacket drain valve 53 and cooling water inlet valve 54. As shown in FIG. 3, and especially in FIG. 4, cooling water is introduced through pipe 56 tangentially into pipe 57 so that it swirls around conduit 45 and has no tendency to enter riser tube 42. As is evident, pipe 56 could be introduced directly into jacket 12 at a point below conduit 45 so that there would be no tendency for cooling water to run back down riser tube 42.

When cooling water is introduced into jacket 12 the temperature of the vessel drops to dispensing temperature within 3 to 4 minutes. Upon reaching dispensing temperature or "holding temperature," the two solenoid valves 53 and 54 close. The jacket water will now circulate by thermosiphon means due to the boiling action caused by the low wattage heater. The controller will then cut the cooling water flow in and out as necessary to maintain the medium in the vessel at the desired level required for the dispensing operation. The temperature band width has been found to hold within ± 0.5°C.

To initiate operation of the apparatus, vessel 11 is filled with water alone to the desired level. Water is introduced into the jacket circuit consisting of jacket space 37, pipe 29, boiler 32 and riser 42 through pipe 56. Water is introduced to a level just short of side arm 57. Valve 23 is opened and cap 58 is "cracked" just enough to allow dispensing arm 59 of valve 23 to partially fill with water. The requisite quantity of agar or other culture medium is then added to the water in vessel 11. Dome 17 is fastened in place using Vee-clamp 21, and the programming unit is switched on which activates heating coils 33 and 34.

As the temperature of the medium 44 is raised, air in solution therein is driven out of solution. As the vapor pressure of the medium increases, the air expelled from the solution and the air in the ullage above the medium are forced out of the vessel by the water vapor. Dome 17 is fitted with element 61 containing a steam trap 62 and a filter element 63. The filter element 63 is hydrophobic and will prevent passage of any air-borne material larger than $0.8\mu$. When steam trap 62 has vented air in the vessel, its temperature will rapidly rise to 100°C, the boiling point of water. Steam trap 62 is so designed that it closes thermostatically at this temperature. The trap remains closed from this time until the sterilization period is completed and cooling has proceeded far enough to drop the temperature of the trap below 100°C. At this point it reopens automatically. This breaks the vacuum in the cooled vessel 11 and permits room air to re-enter the vessel. Since any viral or bacterial material that could possibly enter the vessel through the trap must be air-borne, its particle size must be larger than $1.0\mu$, so that filter 63 will effectively prevent contamination of the sterile medium.

The fact that filter element 63 is hydrophobic makes it possible for air and steam (the latter as gas) to vent through the filter and out through the steam trap. When the steam trap re-opens, only air can pass through the filter into the vessel. Any condensed water present in the trap above the filter, even though it has been sterilized by the local temperature of 121°C, cannot re-enter the vessel through the filter, thus precluding liquid-borne contaminants.

Fixture 64 is a relief valve. A thermometer (not shown) may be inserted into the vessel through port 66, shown in FIG. 2 as covered.

A convenient wattage for heating element 33 is 1350 and for element 34 is 150. During the heat-up phase of the cycle, the total wattage is then 1500. After sterilization temperature is reached, the wattage of heating element 33 is conveniently cut back to about 660. Under on-off control, during the sterilization phase, the heat input to boiler 32 then oscillates between 150 and about 810 W.

Figure 2:
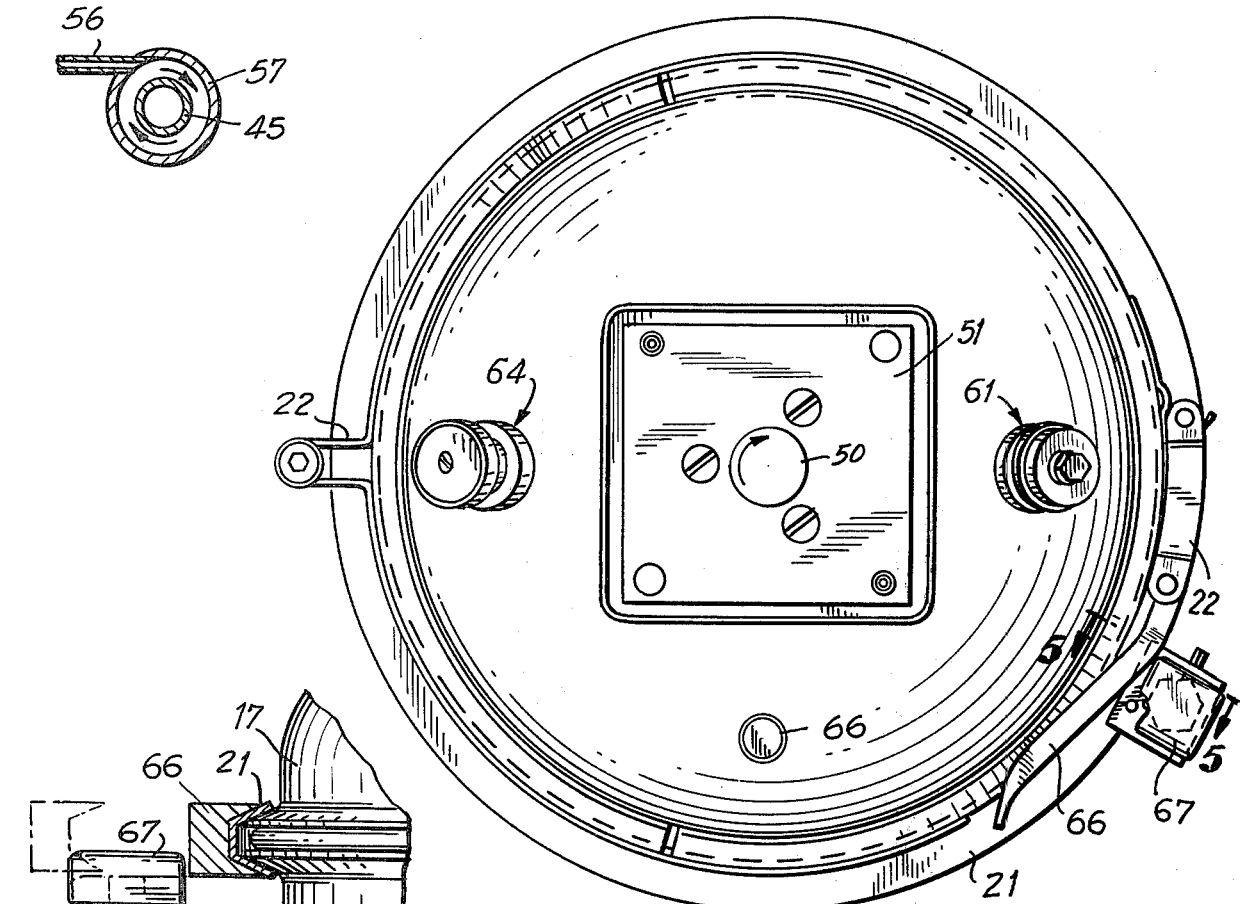
FIG. 2 is a top view of the cover of the sterilization vessel of said apparatus.
Figure 5:
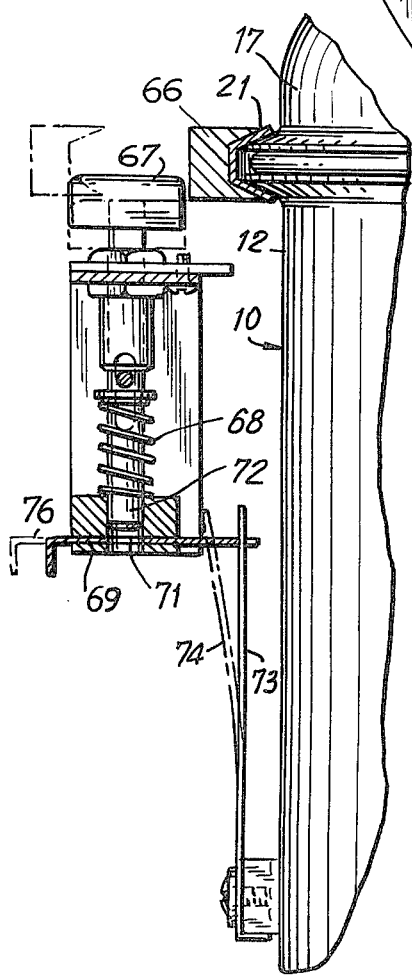
FIG. 5 is a view taken along line 5 — 5 of FIG. 2.

To place Vee-clamp 21 in position handle 66 must be swung in clockwise direction to reach the position shown in FIG. 2. In order to swing the handle in this way, button 67 must be depressed against biasing spring 68. When the system is cold, this can be done because plate 69 having opening 71 therein is positioned so that rod 72 integral with button 67 can pass through opening 71.

When the heating cycle is initiated, bi-metal strip 73 moves toward the position indicated by the dashed lines 74. Bi-metal strip 73 is linked to plate 69 so that as strip 73 moves toward the position 74, plate 69 moves toward the position indicated by the numeral 76. Once opening 71 is out of registry with rod 72, button 67 cannot be depressed. Opening 71 is sized so that button 67 cannot be depressed until the temperature of the jacket falls well below 100°C, under which circumstances there is no longer any danger from super-ambient pressure in the vessel.

When sterilization is complete and the contents of the vessel have been cooled down to holding temperature, usually 46°C, cap 58 can be removed and the contents of the vessel can be dispensed as desired. Alternatively, where the vessel has been used for sterilizing laboratory ware, the vessel can be drained and the ware removed through the top thereof.

Figure 7:
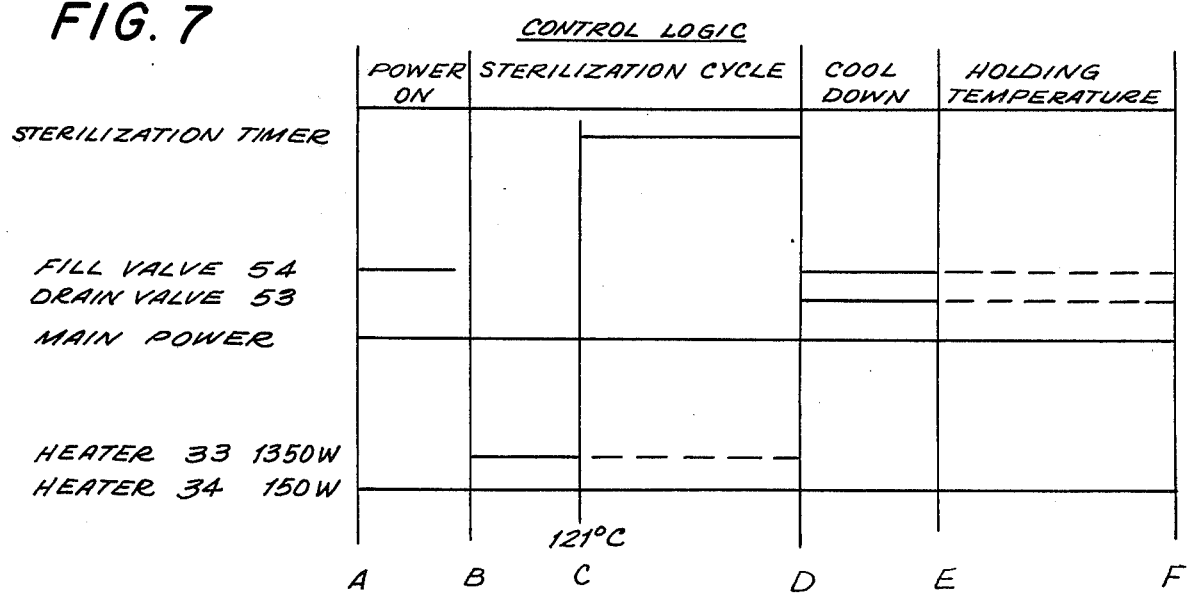
FIG. 7 shows diagrammatically the logic sequence involved in taking the apparatus through a sterilization procedure.

The sequence of operations and control logic in putting the apparatus of the present invention through a sterilization cycle is shown in FIG. 7. Power is turned on at time A and solenoid valve 54 is opened manually to fill the jacket space 37, boiler 32, riser 42 and connecting piping. The programmer 52 is then turned on at time B. The set point for the controller is now 121°C so full power is supplied to both heating coils. When the temperature as indicated by sensor 48 reaches 121°C at time C, a timer is started. Simultaneously the wattage of heater 33 is dropped to about 660, and heater 33 goes into on-off cycling under the control of sensor 48 and controller 47. Time interval CD is selected to appropriate to the sterilization temperature. For a temperature of 121°C, CD is usually about 15 minutes, and is preset in the timer. At time D the timer switches the set point for controller 47 to a new dispense temperature setting (46°– 52°C), turns off heater 33 and opens solenoid valves 53 and 54 for transferring cooling liquid through the jacket. The cooling down period DE lasts for 3 – 4 minutes. Also at time D, the high wattage heater 33 is turned off completely but low wattage heater 34 stays on pumping boiling water at low rate into the jacket.

Periodically, as needed, solenoid valves 33 and 34 are opened to pass cooling water through jacket 37 in accordance with signal from sensor 48 to controller 47. During the period EF the temperature is controlled to maintain the culture medium in liquid state, and portions of culture medium can be withdrawn through dispensing valve 23.

It will be recognized that even where the vessel is of the size described herein, a wide variety of methods of controlling the heat input to boiler 32 may be employed. Thus, the heat input could be larger than 1500 W, more than two heating coils could be used and the relative wattages of the two heating coils could be different. Further, the degree to which the wattage of heater 33 is cut back once the sterilization temperature has been reached could be varied as could the means of cutting back the wattage. As is evident, it is not necessary to use phase control for reducing the wattage of heating coil 33. Introduction of a step-down transformer would effect the same purpose. Also, while the combination of a sensor with a bridge circuit gives unusual sensitivity of control and therefore unusual precision of control, other means are also available. However, the ram effect described herein makes it possible to elminate the use of usual circulating pump while providing unusually rapid circulation of heating fluids. Moreover, the close spacing between the interior of the jacket and the exterior of the vessel provides for unusually rapid flow of the heating fluid around the exterior of the vessel, thereby cutting the resistance to heat transfer of the stagnant liquid film at the exterior of the vessel.

It would be possible to operate the temperature control system in a mode where heater 34 is cut-off completely when cooling water is introduced into the jacket. However, by keeping heater 34 on at all times, deviations from the set point are minimized.

Obviously, where larger vessels are to be put through a sterilization cycle as described herein, the wattage required for the boiler 32 will be commensurately larger and the dimensions of riser 42 and cooling water inlet pipe, etc., will also be larger. However, such changes are well within the skill of one versed in the art.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. Apparatus for taking a container and the contents thereof through a timed temperature cycle comprising:
    a. a vessel having top and bottom portions;
    b. a jacket joined to said vessel and enclosing with said vessel a narrow jacket space therebetween, said jacket having top and bottom portions;
    c. boiler means including heating means;
    d. column means joining said boiler means to said jacket proximate the top thereof for carrying boiling water and steam from said boiler means to said jacket near the top thereof and into said jacket space for heating said vessel and any contents therein;
    e. guiding means for leading said water through said jacket space to the bottom of said jacket in a path such that said water makes contact with a major portion of the exterior of said vessel;
    f. conduit means joining said jacket proximate the bottom thereof to said boiler means for returning said water from proximate the bottom of said jacket to said boiler means;
    g. first pipe and valve means for introducing cooling water into said jacket near the top thereof;
    h. second pipe and valve means for draining water from said jacket;
    i. temperature sensing means in said vessel, said sensing means being adapted for transmitting a signal corresponding to the temperature of said vessel; and
    j. programmable control means constructed and arranged for receiving said signal from said temperature-sensing means, controlling heat output by said heating means and flow of said cooling water in response to said signal and an imposed timed-temperature program.

2. The apparatus as defined in claim 1 further comprising:
    k. programming means operatively connected to said controller for taking said vessel through a timed-temperature program.

3. The apparatus as defined in claim 1, wherein said vessel is fitted with a cored dispensing valve, the core of said valve being connected to said jacket and conduit means for traversal of heated and cooling water therethrough.

4. The apparatus as defined in claim 1, wherein said jacket has joined thereto an adjustable pressure-relief valve, the circuit comprised of said jacket space, boiler means, conduit means and column means being sealed except for said pressure-relief valve, said pressure relief valve being designed to vent water and air when the pressure exceeds a preselected value.

5. The apparatus as defined in claim 4, further comprising a first cover for said vessel, means for sealing said first cover to said vessel, agitating means mounted on said first cover for stirring any contents in said vessel, a thermostatic steam trap mounted on said first cover for venting air from said vessel, said trap being adapted for closing when heated by steam, and a hydrophobic filter which prevents passage of water and of particles larger than about $0.8\mu$, thereby preserving said contents from contamination by water droplets, bacteria or particle-borne viruses.

6. The apparatus as defined in claim 1, wherein said heating means consists of a first electrical resistor of high wattage and a second electrical resistor of low wattage.

7. The apparatus as defined in claim 1, wherein said column means is essentially vertical.

8. The apparatus as defined in claim 1, wherein the impedance to flow of a mixture of boiling water and steam is lower for said column means than for said conduit means.

9. The apparatus as defined in claim 1, wherein said apparatus further includes conical means joining said column means with said boiler means with a gap therebetween for flow of water from said conduit means into said boiler means.

10. The apparatus as defined in claim 6, wherein said controller has step-down means therein for reducing the wattage of said first resistor to a second lower value which is higher than that of said second resistor and which, in combination with said second resistor exceeds the wattage needed to hold said vessel at the maximum temperature desired.

11. The apparatus as defined in claim 5, wherein said sealing means comprises a flange on said vessel, a mating flange on said cover, a gasket therebetween and clamp means for biasing said vessel flange and said cover flange against said gasket.

12. The apparatus as defined in claim 10, wherein said clamp means includes a toggle-locking handle which releases said clamp means when said handle is swung outwardly from said vessel and said apparatus further comprises a safety lock for said clamp means to prevent opening of said clamp means when said vessel is at a temperature above about 100°C, said safety lock including a bi-metal strip attached to said jacket and having an end which moves in response to temperature change in said jacket, a plate operatively linked to said movable end, said plate having an opening therein, a rod mounted for axial displacement, said rod having first and second ends, biasing means holding said rod in a position such that said first end prevents displacement of said handle outwardly, said rod being positioned relative to said opening in said plate so that when the temperature of said jacket is below about 100°C, said rod can be displaced axially to pass said second end thereof through said opening and remove said first end from blocking position and thereby permit outward movement of said handle and removal of said clamp means, said opening being so sized and located in said plate that movement of said bi-metal strip as the result of said jacket temperature being above 100°C displaces said plate sufficiently so that said second end of said rod is prevented from passing through said opening, thereby preventing movement of said handle outwardly and premature opening of said clamp means and removal of said first cover.

13. The apparatus as defined in claim 1, further comprising a second cover having mounted thereon a thermostatic steam trap which closes when heated by steam and a hydrophobic filter which allows air to vent from said vessel and to re-enter said vessel but which prevents the passage of water and of particles larger than about $0.8\mu$, thereby preserving any contents in said vessel from contamination by water droplets, bacteria or particle-borne viruses, said second cover being suitable for use when sterilizing laboratory ware.

14. The apparatus as defined in claim 13, wherein said clamp means includes a toggle-locking handle which releases said clamp means when said handle is swung outwardly from said vessel and said apparatus further comprises a safety lock for said clamp means to prevent opening of said clamp means when said vessel is is at a temperature above about 100°C, said safety lock including a bi-metal strip attached to said jacket and having an end which moves in response to temperature change in said jacket, a plate operatively linked to said movable end, said plate having an opening therein, a rod mounted for axial displacement, said rod having first and second ends, biasing means holding said rod in a position such that said first end prevents displacement of said handle outwardly, said rod being positioned relative to said opening in said plate so that when the temperature of said jacket is below about 100°C, said rod can be displaced axially to pass said second end thereof through said opening and remove said first end from blocking position and thereby permit outward movement of said handle and removal of said clamp means, said opening being so sized and located in said plate that movement of said bi-metal strip as the result of said jacket temperature being above 100°C displaces said plate sufficiently so that said second end of said rod is prevented from passing through said opening, thereby preventing movement of said handle outwardly and premature opening of said clamp means and removal of said first cover.

15. The apparatus as defined in claim 1, wherein said jacket is spaced from said vessel by wire means tack-welded to the periphery of said vessel in helical form.

16. The apparatus as defined in claim 15, wherein said wire means is from 0.0625 to 0.1875 inch in diameter.

17. The apparatus as defined in claim 15, wherein the distance between turns in said helix is between 1 and 2 inches.

18. The apparatus as defined in claim 15, wherein said helix is brazed to the interior wall of said jacket and said jacket and said vessel are brazed together proximate the tops thereof.

* * * * *